United States Patent
Rogala et al.

(10) Patent No.: US 12,376,867 B2
(45) Date of Patent: Aug. 5, 2025

(54) UNIT FOR THE REAMING OF THE SURFACE OF JOINT CARTILAGE AND OF PERIARTICULAR BONE OF AN ACETABULUM AND FEMORAL HEAD

(71) Applicant: INDYWIDUALNA SPECJALISTYCZNA PRAKTYKA LEKARSKA W MIEJSCU WEZWANIA PIOTR ROGALA, Poznan (PL)

(72) Inventors: Piotr Rogala, Poznan (PL); Jan Rogala, Poznan (PL); Stanislaw Rogala, Poznan (PL); Pawel Zawadzki, Witobel/Steszew (PL)

(*) Notice: Subject to any disclaimer, the term of this patent is extended or adjusted under 35 U.S.C. 154(b) by 463 days.

(21) Appl. No.: 17/779,050

(22) PCT Filed: Jan. 29, 2020

(86) PCT No.: PCT/PL2020/000006
§ 371 (c)(1),
(2) Date: May 23, 2022

(87) PCT Pub. No.: WO2021/112698
PCT Pub. Date: Jun. 10, 2021

(65) Prior Publication Data
US 2023/0000499 A1    Jan. 5, 2023

(30) Foreign Application Priority Data

Dec. 2, 2019 (PL) ...................................... P.432041
Dec. 2, 2019 (PL) ...................................... P.432044

(51) Int. Cl.
*A61B 17/16* (2006.01)

(52) U.S. Cl.
CPC ...... *A61B 17/1666* (2013.01); *A61B 17/1617* (2013.01); *A61B 17/1659* (2013.01); *A61B 17/1668* (2013.01)

(58) Field of Classification Search
CPC ............ A61B 17/1666; A61B 17/1617; A61B 17/1659; A61B 17/1668
(Continued)

(56) References Cited

U.S. PATENT DOCUMENTS 6,283,971 B1 * 9/2001 Temeles ............. A61B 17/1666
                                                              606/81
6,755,865 B2 * 6/2004 Tarabishy ................. A61F 2/34
                                                              606/81
(Continued)

FOREIGN PATENT DOCUMENTS

WO    2009023972 A1    2/2009
WO    2011075742 A1    6/2011

OTHER PUBLICATIONS

International Search Report for corresponding PCT/PL2020/000006, dated Aug. 20, 2020.
(Continued)

*Primary Examiner* — Jessica Weiss
(74) *Attorney, Agent, or Firm* — Egbert, McDaniel & Swartz, PLLC (57) ABSTRACT

Disclosed is a unit for reaming of the surface of joint cartilage and of periarticular bone of an acetabulum and femoral head, used in orthopaedical surgery, being used as equipment to prepare the surface of cartilage and periarticular bone for endoprosthesis implantation. The unit is has at least two burrs with a slanting end of the cutting blade and an arc shape, ending with a ball-shaped pivot, placed in the guides of a matrix, whereas each of the burrs is placed in a (Continued)

channel of a shaped body, whereas the body is connected by a joint with the unit's drive mechanism.

9 Claims, 8 Drawing Sheets

(58) Field of Classification Search
USPC .................................................... 606/81–89
See application file for complete search history.

(56) References Cited

U.S. PATENT DOCUMENTS

| | | | | |
|---|---|---|---|---|
| 6,918,914 | B2 * | 7/2005 | Bauer | ................ A61B 17/1666 606/81 |
| 7,608,076 | B2 | 10/2009 | Ezzedine | |
| 9,414,850 | B2 * | 8/2016 | Cleveland | .......... A61B 17/1659 |
| 9,610,084 | B2 * | 4/2017 | Walker | ................ A61B 17/1666 |
| 2005/0154398 | A1 * | 7/2005 | Miniaci | ............... A61B 17/1668 606/80 |
| 2005/0203525 | A1 | 9/2005 | Patrick et al. | |
| 2006/0217730 | A1 | 9/2006 | Termanini | |
| 2006/0276797 | A1 * | 12/2006 | Botimer | ............. A61B 17/1617 606/81 |
| 2007/0016211 | A1 | 1/2007 | Botimer | |
| 2011/0152868 | A1 * | 6/2011 | Kourtis | ................ A61B 17/025 606/80 |
| 2011/0202060 | A1 | 8/2011 | White et al. | |
| 2015/0196402 | A1 * | 7/2015 | Kim | ..................... A61F 2/4609 606/81 |
| 2018/0132866 | A1 | 5/2018 | Muller | |

OTHER PUBLICATIONS

Written Opinion of the International Searching Authority for corresponding PCT/PL2020/000006, dated Aug. 20, 2020.

* cited by examiner fig. 1 fig. 2 fig. 3 fig. 4 fig. 7 fig. 6 fig. 5 fig. 8 fig. 9 fig. 12 fig. 11 fig. 10

UNIT FOR THE REAMING OF THE SURFACE OF JOINT CARTILAGE AND OF PERIARTICULAR BONE OF AN ACETABULUM AND FEMORAL HEAD

The subject of the invention is a unit for the reaming of the surface of joint cartilage and of periarticular bone of an acetabulum and femoral head, used in orthopaedical surgery, being used as equipment to prepare the surface of cartilage and periarticular bone for endoprosthesis implantation.

Current solutions are based on a set of burrs limited by graded, fixed diameters and a wide range of equipment used during procedures. The drawback of these solutions is a large number of elements used in the surgical set, which frequently remain unused during the procedure. The currently used tools do not allow for a controlled removal of the products of cutting out of the operating field.

Units are known for the reaming of internal surfaces of joints, in particular of the hip joint, and so: in the US patent description US2006217730 an improved spring-loaded expandable acetabular reamer is described, which comprises a number of convex reaming segments symmetrically located by pair around a central core of the Reamer tool. It is also a goal of the present invention to provide and improve a spring-loaded reaming segment, which expands faster and requires less manipulation by the operating surgeon and staff, therefore minimizing the risk of infection and of tissue damage. Furthermore, introducing large size conventional acetabular reamers with rough and sharp edges through small surgical incisions will undoubtedly cause damage to the edge of the incision and to the surrounding soft tissues, which may ultimately result in delayed wound healing.

The U.S. Pat. No. 6,918,914 demonstrates an acetabular reamer including a reaming head having arcuately-shaped segments generally symmetrically distributed about a center point. The arcuately-shaped segments are extendable or retractable about the center point to create a variable dimensioned recess in an acetabular region. The reamer may also include an actuator for selectively extending or retracting the segments so that the segments remain generally symmetrically distributed about the center point as the segments are expanded or retracted. The segments may further include cutting surfaces having a shape corresponding to a portion of a surface of a hemisphere. In one form, the segments may be configured in a narrow symmetrical "slice" of a hemispherical surface that provides an adjustable hemispherically shaped cutting arc, whereas the U.S. Pat. No. 7,220,264 describes reamer for reaming of a acetabulum during a minimally invasive procedure. Generally, the reamer, particularly the reamer head, can be inserted and removed through a substantially small incision without trauma to the tissue surrounding the incision. The reamer, generally includes a reaming or scraping portion, which are aligned substantially along a single meridian of a hemisphere. The reamer further includes stabilizing portions to assist in ensuring a selected reaming orientation.

In the US2006264958/U.S. Pat. No. 7,608,076 the use of a surgical reamer for the cutting of cartilaginous and bone tissue is demonstrated. The reamer further includes a fixed support portion aligned with the drive axis and having at least one radial cutting blade, a pivoting portion aligned with the drive axis and pivotable about this axis, the pivoting portion supporting at least one radial cutting blade and a pivoting joint wherein the pivoting portion may be pivoted toward and away from the fixed portion so as to expand or contract the reamer in relative overall size.

In the US2005203525(A1) patent an acetabular reamer was described with a cutting structure rotatable about a longitudinal axis with a domed shell portion. The shell has an outer surface presenting multiple cutting sites and an inner surface for accumulation of debris. The tool shape is defined by a pair of first curved portions generated about a first radius with a center that lies on the axis and a pair of second curved portions generated about a center that is spaced apart from the axis.

In the US2006276797 (A1) patent discusses an expanding reamer for reaming or cutting a concave surface, for example, for reaming an acetabulum in preparation for implanting a prosthetic component, such as an acetabular cup or socket, during a hip arthroplasty. The reamer includes a rotating shaft cooperating with a surgical drill or other power source at one end and rotating a reamer head at the other end, and a system adapted to expand one or more blades on the reamer head. In a preferred version, the reamer head comprises a plurality of generally circular, preferably substantially flat and parallel blades, the outer blades of which are radially expandable as segments of a cutting sphere to enlarge the effective diameter of the reamer head. The US2007016211(A1) patent discusses an expanding reamer for reaming or cutting a concave surface, for example, for reaming an acetabulum in preparation for implanting a prosthetic component during a hip arthroplasty. A rotating shaft cooperates with a surgical drill or other power source at one end and rotates a reamer head at the other end, and an actuation system expands one or more blades on the reamer head. The reamer head comprises one or more cutting blades, which act as segments of a cutting sphere, wherein the blades are expandable in directions non-parallel to the plane of the respective blades in order to enlarge the cutting sphere. Upon rotation of the reamer head, the blade(s) form a portion of an effective cutting sphere that is preferably greater-than-180-degrees; this allows greater flexibility in placement of the shaft of the reamer relative to the surface being reamed, for example, relative to the center of axis of the acetabulum. In the US2011202060 (A1) patent a disposable acetabular reamer designed to improve tissue removal efficiency is described. The reamer device comprises a reamer cutting shell and a reamer driver interface. The reamer cutting shell has a hemispherical structure with a plurality of spaced apart rib portions that extend from a central region located about an apex of the shell.

The essence of the invention is a unit for reaming of the surface of joint cartilage and of periarticular bone of an acetabulum and femoral head, characterised by that it has at least two burrs with a slanting end of the cutting blade and an arc shape, ending with a ball-shaped pivot, placed in the guides of a matrix, whereas each of the burrs is placed in a channel of a shaped body, whereas the body is connected by a joint with the unit's drive mechanism, whereas the matrix is placed on a shank, which is connected with the shaft by a threaded connection with a stop, and the body has a threaded joint to the shaft.

It is advantageous when the body has a chamber for securing the reamed bone and when the body has an external supporting surface for inserting into the acetabulum of the reamed bone and protecting the bone tissue against damage.

It is also advantageous when each burr is placed at the same angular distance from a circular plane perpendicular to its lengthwise axis and when the burrs are bevelled at an angle $\beta$ 40-50° advantageously 45°.

It is also advantageous when the angle of application $\alpha$ of the burr blades to the surface being reamed is within a range of 5-15° advantageously 10°.

It is especially advantageous when the cutting edge of the burr has a cutting tongue.

Moreover it is advantageous when the burr is a tube or an open element, or a partially open element.

It is advantageous when each of the burrs has an outlet opening of the duct used to clean the inside of the burr.

The use of the solution presented in the invention enables the following technical and utility effects:
- the possibility of precise machining of acetabulum surfaces without needing a full resection, like in the case of conventional solutions,
- reducing the invasiveness of the surgery,
- the possibility of using customized joint endoprostheses,
- geometry, placement and movement of the cutting blades enables the removal of cuttings out of the operating field, which ensures higher sterility and visibility of the area undergoing surgery.
- the possibility of obtaining a continuously variable cutting diameter, adapted to the diameter of the machined acetabulum,
- obtaining a high degree of machining precision,
- obtaining a high smoothness of the machined surface.

The subject of the invention, in the example implementation, which is not limiting, was presented on drawings, where FIG. 10 presents a view of the blade being partially open, FIG. 11 presents detail A from FIG. 10, whereas

A unit for the machining of external surfaces of joint bones, being the head, has at least two burrs 2 with a slanting end of the cutting blade 16 and an arc shape, ending with a ball-shaped pivot 10, placed in the guides 11 of a matrix 3. Each of the burrs 2 is placed in a channel 12 of the shaped body 1. The body 1 is connected by a joint with a drive mechanism 6 of the unit, whereas the matrix 3 is placed on a shank 13 having a threaded connection 18 with a stop 8 to the shaft 4, and the body 1 has a threaded joint 17 to the shaft 4. Each of the burrs 2 is placed at the same angular distance from a circular plane perpendicular to its lengthwise axis. Burrs 2 are bevelled at an angle β 45°, whereas the a angle of application of the cutting blades 16 of the burrs 2 to the machined surface 26 has a value of 10°. The cutting blade 16 of the burr 2 has a cutting tongue 19 for breaking the matter being cut. There are versions where the burr 2 is a tube, there are also versions where the burr 2 is an open element, there are also versions where the burr 2 is a partially open element. Each of the burrs 2 in the first version has an outlet opening 23 of the burr duct 24 used to clean the inside of the burr 2.

Figure 1:
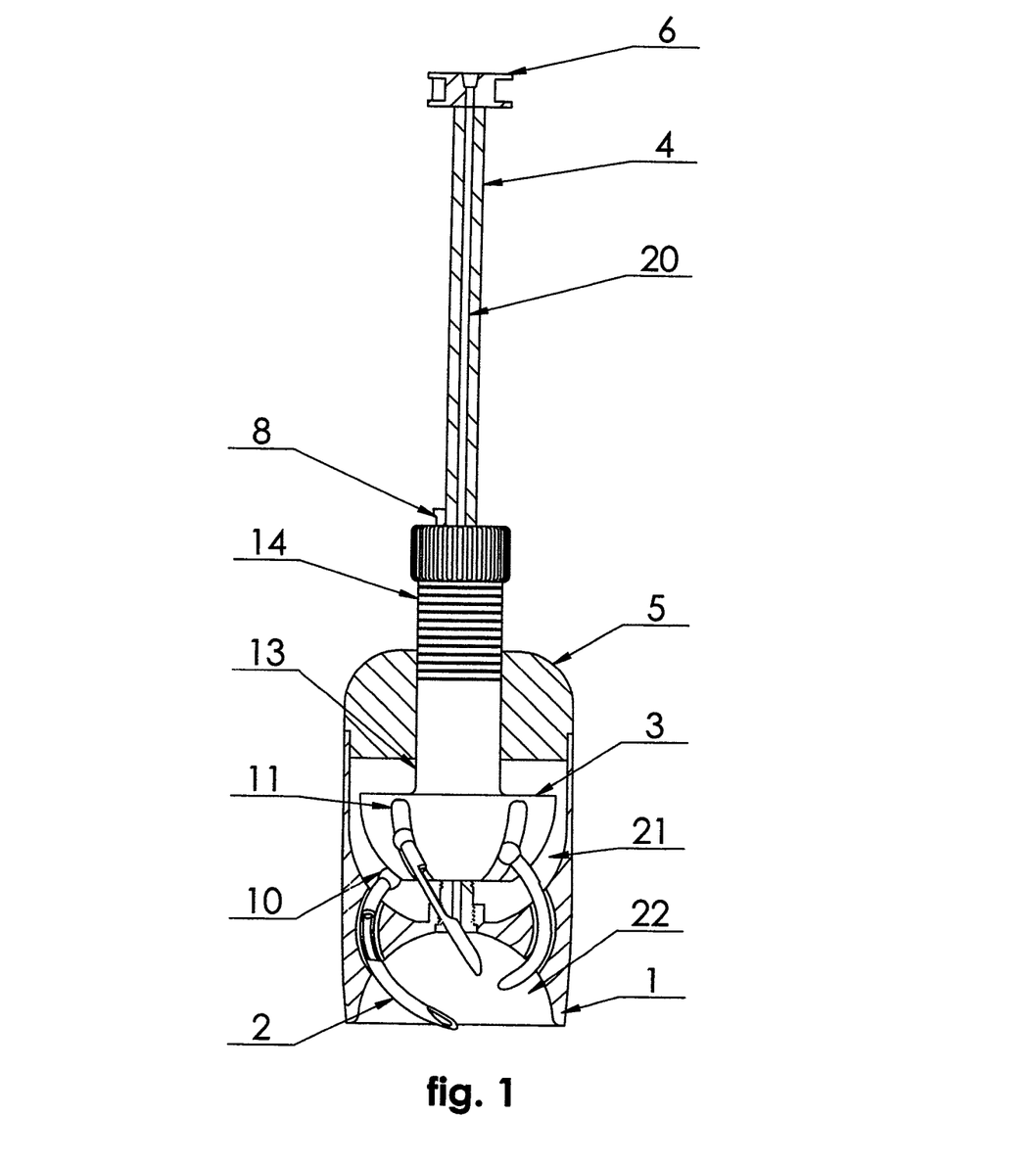
FIG. 1 presents the cross-section of the unit on a plane passing through its axis of rotation for the machining of the femoral head in the first version.
Figure 2:
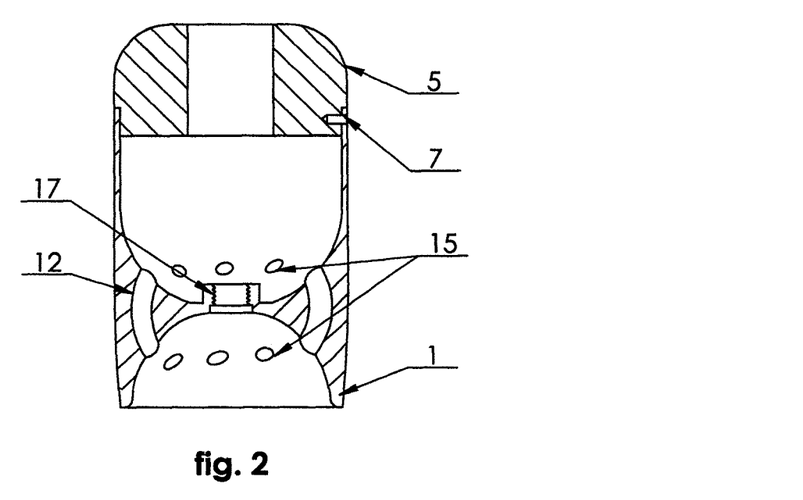
FIG. 2 presents the cross-section of the body on a plane passing through its axis of rotation for the machining of the femoral head in the first version.

The drive mechanism 6 is permanently connected with the matrix 3 by the shaft 4 which transfers the rotational drive. The matrix 3 is moved in a reciprocating and rotational manner by a threaded connection 14 with the shaft 4. In the matrix 3 the burrs 2 with the cutting blades 16 move inside the ducts 12 of the body 1. Each of the burrs 2 moves through the ducts 12, which force it to move solely over a specific trajectory. The cutting blades 16 of the burr 2 are connected to the matrix 3 using a movable connection through a ball-shaped pivot 10 and guide 11 which ensure their minimal movement in relation to the matrix 3 and body 1.

The drive mechanism 6 is connected to an external rotating drive. By connecting the drive mechanism 6 with the shaft 4 the rotating movement is transferred to the entire tool. During work the tool is rotating around the axis of the shaft 4—a stipulated axis of symmetry of the tool. The movement is either clockwise or counterclockwise, depending on the angular setting of cutting blades 16. The shaft 4 is connected by the threaded connection 18 to the body 1. Both connections with the body 1 and the drive mechanism 6 have a thread that is in agreement with the tool's direction of rotation, which prevents the possible disconnection of the parts. On the shaft 4 the matrix 3 is screwed on, moving over a thread with a high pitch, which ensures high linear displacement and low angular displacement. The movement of the matrix 3 is locked by the stop 8—wedge 9 system. After setting the matrix 3 to the dimension of the cutting area 25 of the joint by turning it around the tool's axis of symmetry with the widened part of the shaft 4 with incisions facilitating gripping, its movement is locked by screwing in the stop 8 into the threaded hole 15 located in the matrix 3. Screwing in the stop 8 results in the gradual driving of the bottom surface of the wedge 9 into the non-threaded surface of the shaft 4. Gradual screwing in of the stop 8 at some point becomes impossible, which means that the wedge 9 resting against the surface of the shaft 4 has completely locked the movement of the system of the stop 8 with the matrix 3 In order to release the movement of the matrix 3 the stop 8 should be screwed out of it. The matrix 3 moves within the chamber of the body 1 limited by the walls of the body 1 and two parts of the cover 5 of the body 1. The cover 5 of the body 1 restricts the maximum external protraction of the matrix 3, additionally stabilising the position of the matrix 3 in relation to the tool's axis of symmetry. The cover 5 of the body 1 is bolted to the body 1 with a set of four mounting bolts 7. The rotational and linear movement of the matrix 3 in relation to the shaft 4 causes the head of the matrix 3 to press on the spherical ends of the cutting blades 16 of the burr 2. The ends of the cutting blades 16 of the burr 2 in the shape of the ball-shaped pivot 10 set on the threader rod and screwed into the body 1 move within the channels 12 cut in the surface of the head of the matrix 3. The guides 11 are cut symmetrically or asymmetrically in relation to the tool's axis of rotation—this depends, among others, on the number of cutting blades 16. The guides 11 restrict the movement of the cutting blades 16. Screwing the matrix 3 out of the body 1 in relation to the shaft 4 results in the cutting blades 16 of the burr 2 sliding into the closed chamber of the body 1 at an angle of 45°. Screwing the matrix 3 in has a reverse effect. The cutting blades 16 of the burr 2 slide out, making the cutting edges closer to each other, which results in the decrease of the final diameter of the machined spherical surface. The movement of the cutting blades 16 of the burr 2 outside of the guides 11 cut in the head of the matrix 3 takes place within the space restricted by the openings 15 in the body 1. Channels 12 ensure the movement of the cutting blades 16 of the burr 2 over an arc-shape trajectory with a defined radius. After establishing an appropriate diameter of machining—that is, the position of the cutting blades 16 of the burr 2 and locking the movement of the matrix 3 with the stop 8, the drive mechanism 6 is used to provide rotational movement from an external drive. The angle of application α of the cutting blade 16 of the matrix 3 has a value of 10°, and the angle of attack β 45°. The cuttings fall into the ducts 24 of the burr 2, falling out between the internal chamber 21 and the external chamber 22 of the body 1 through the outlet opening 23 of the duct 24 used to clean the inside of the burr 2. Along the shaft 4 and through the drive mechanism 6 a duct for a medium 20 (e.g. water) passes, which enables the delivery of a medium to the internal space of the body 1, diluting the cuttings and aiding in their removal.

After establishing the position (cutting diameter) of the matrix 3, the matrix 3 is locked by screwing in the stop 8 with the wedge 9, after which the drive is started. Afterwards, the tool is applied to the machined surface, e.g. the hip joint, and the medium is fed through the duct 20 located along the shaft 4 and in the drive mechanism 6, after which the surface is cut with the cutting blades 16 of the burr 2. The cuttings with the medium fall out through the outlet openings 23 of the burr ducts 24. Bigger pieces of the cuttings are broken by the cutting tongue 19. After removing a specified amount of matter from the hip joint the position of the matrix 3 is corrected by unlocking the clamp of the drive mechanism 6. After making the changes, inspecting the machined surface, e.g. the hip joint after removing another layer of the hip joint tissue, the matrix 3 is locked again and the material is again removed until required hip joint surface is obtained. The cutting area is limited by the external edges of the tool.

A unit for the machining of external surfaces of joint bones, being the acetabulum, has at least two burrs 2 with a slanting end of the cutting blade 16 and an arc shape, ending with a ball-shaped pivot 10, placed in the guides 11 of a matrix 3. Each of the burrs 2 is placed in a channel 12 of the shaped body 1. The body 1 is connected by a joint with a drive mechanism 6 of the unit, whereas the matrix 3 is placed on a shank 13 having a threaded connection 18 with a stop 8 to the shaft 4, and the body 1 has a threaded joint 17 to the shaft 4. Each of the burrs 2 is placed at the same angular distance from a circular plane perpendicular to its lengthwise axis. Burrs 2 are bevelled at an angle β 49, whereas the angle of application α of the cutting blades 16 of the burrs 2 to the machined surface 26 has a value of 10°. The cutting blade 16 of the burr 2 has a cutting tongue 19 for breaking the matter being cut. There are versions where the burr 2 is a tube, there are also versions where the burr 2 is an open element, there are also versions where the burr 2 is a partially open element. Each of the burrs 2 in the first version has an outlet opening 23 of the burr duct 24 used to clean the inside of the burr 2.

Figure 3:
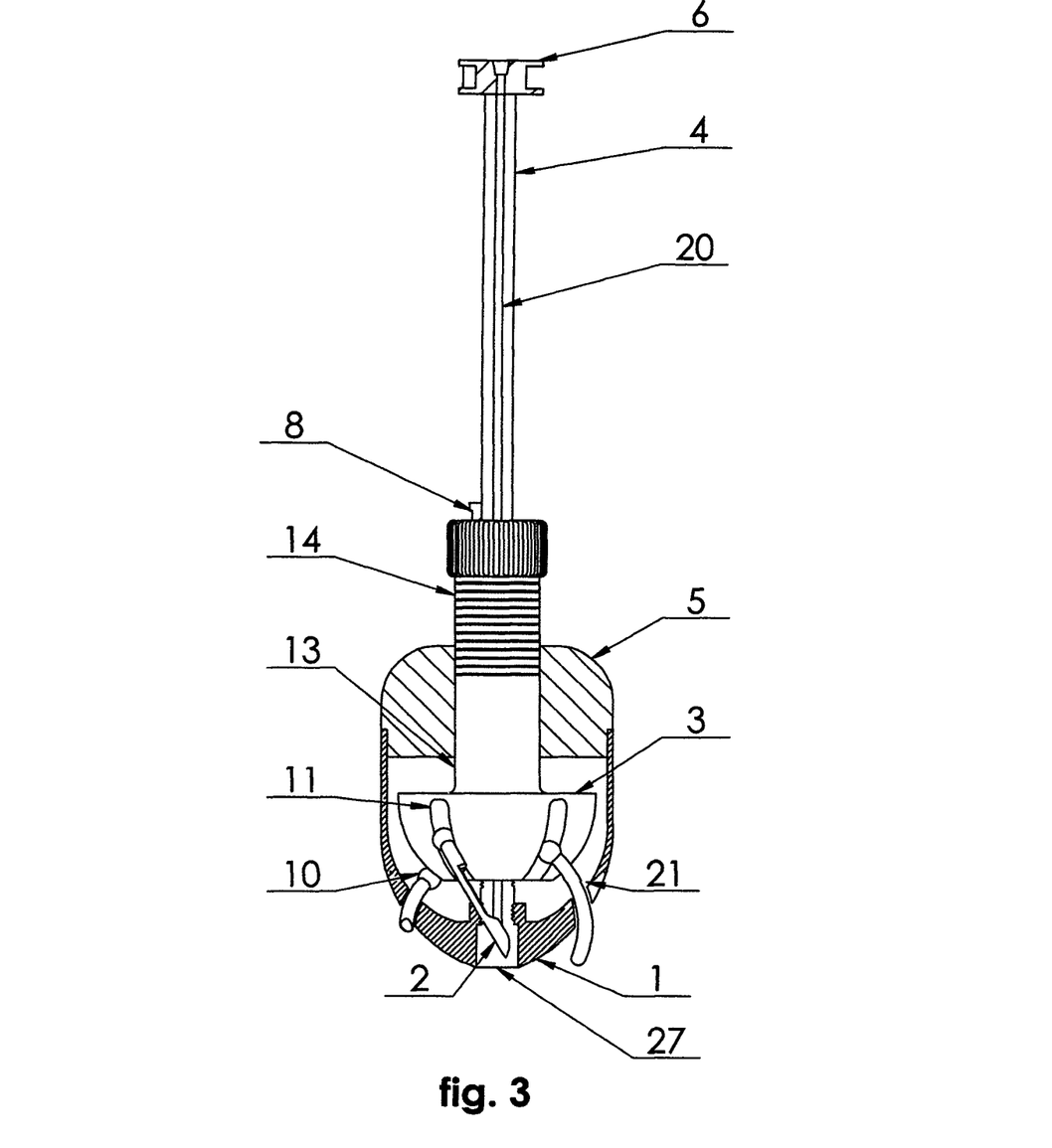
FIG. 3 presents the cross-section of the unit on a plane through its axis of rotation for the machining of the acetabulum in the second version.
Figure 4:
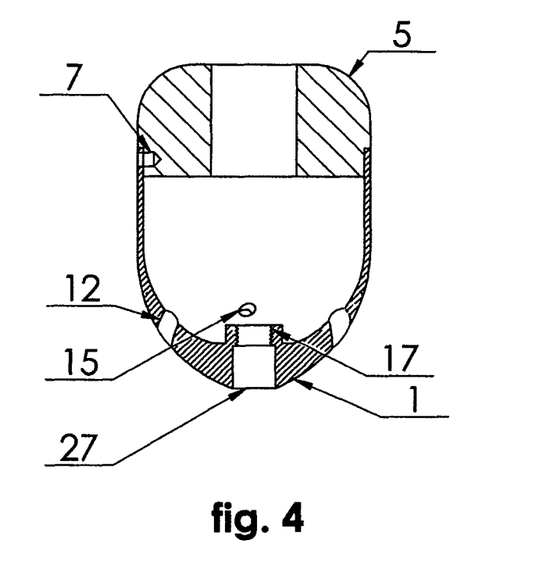
FIG. 4 presents the cross-section on a plane through its axis of rotation for the machining of the acetabulum in the second version.
Figure 5:
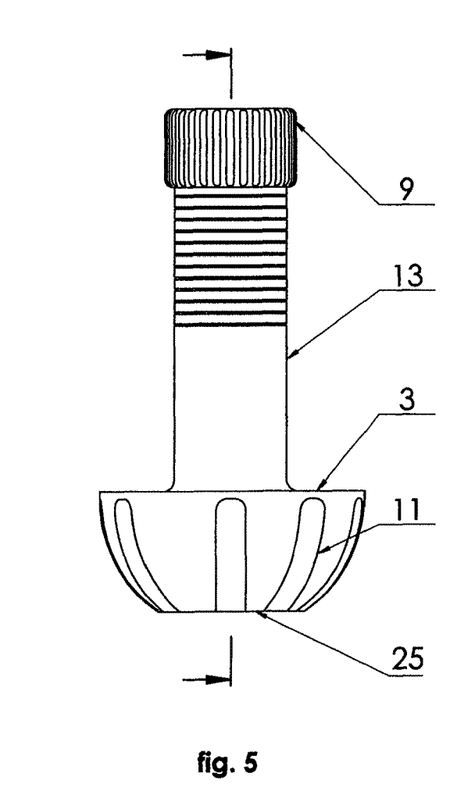
FIG. 5 presents a view of the matrix.
Figure 6:
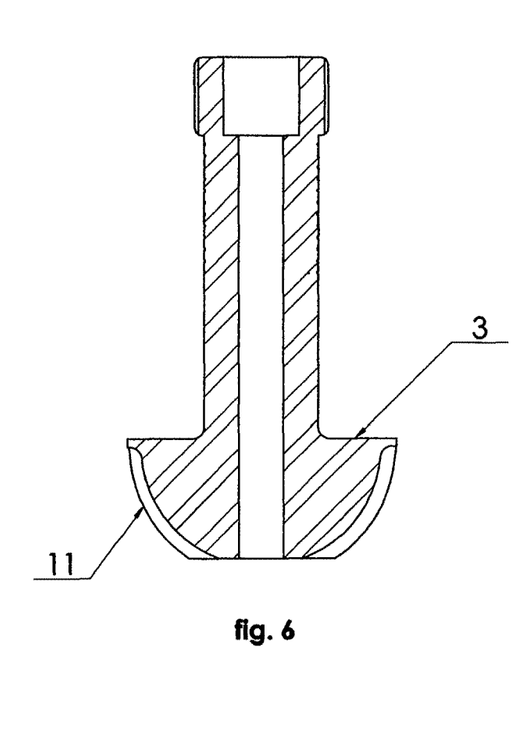
FIG. 6 presents a cross-section of the matrix on a plane perpendicular to its lengthwise axis.
Figure 7:
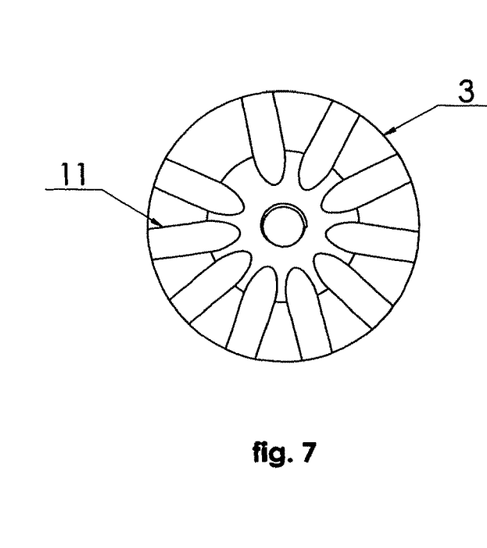
FIG. 7 presents a view of the matrix on a plane through its lengthwise axis.
Figure 8:
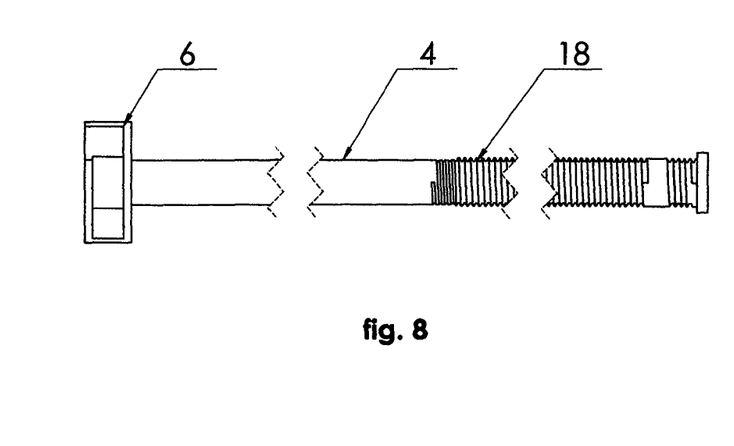
FIG. 8 presents a view of the shaft.
Figure 9:
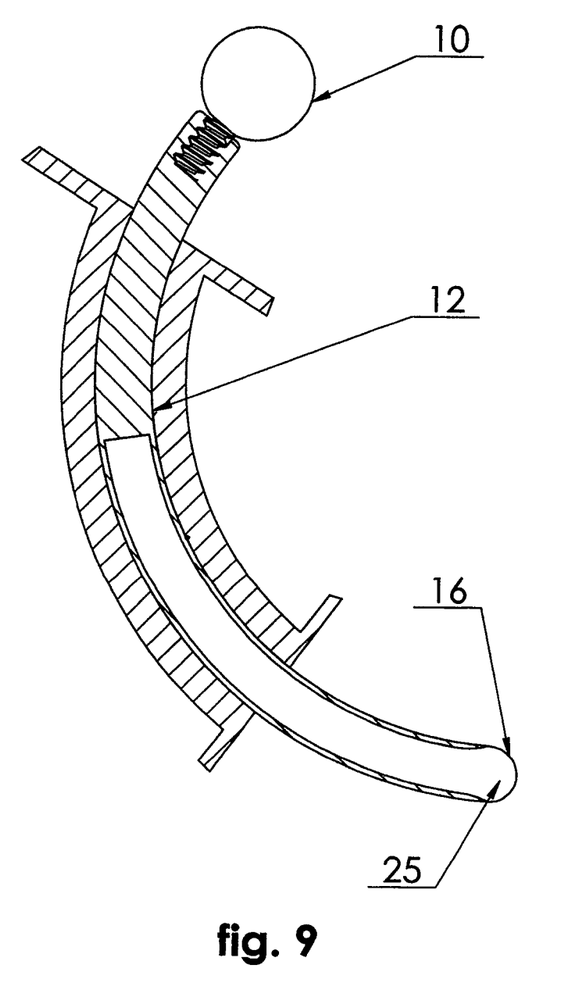
FIG. 9 presents a partial cross-section through the matrix on a plane through the axis of the channel with the blade.
Figures 10, 11:
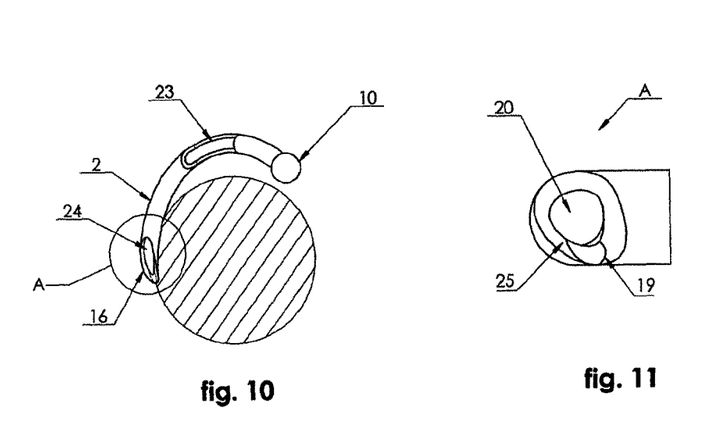
Figure 12:
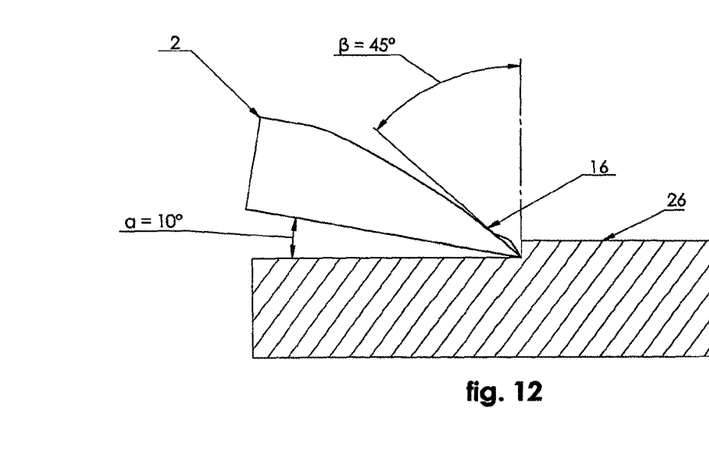
FIG. 12 presents the placement of the burr blade against the machined surface.

The drive mechanism 6 is permanently connected with the matrix 3 by the shaft 4 which transfers the rotational drive. The matrix 3 is moved in a reciprocating and rotational manner by a threaded connection 14 with the shaft 4. In the matrix 3 the burrs 2 with the cutting blades 16 move inside the channels 12 of the body 1. Each of the burrs 2 moves through the channels 12, which force it to move solely over a specific trajectory. The cutting blades 16 of the burr 2 are connected to the matrix 3 using a movable connection through a ball-shaped pivot 10 and guide 11 which ensure their minimal movement in relation to the matrix 3 and body 1.

The drive mechanism 6 is connected to an external rotating drive. By connecting the drive mechanism 6 with the shaft 4 the rotating movement is transferred to the entire tool. During work the tool is rotating around the axis of the shaft 4—a stipulated axis of symmetry of the tool. The movement is either clockwise or counterclockwise, depending on the angular setting of cutting blades 16. The shaft 4 is connected by the threaded connection 18 to the body 1. Both connections with the body 1 and the drive mechanism 6 have a thread that is in agreement with the tool's direction of rotation, which prevents the possible disconnection of the parts. On the shaft 4 the matrix 3 is screwed on, moving over a thread with a high pitch, which ensures high linear displacement and low angular displacement. The movement of the matrix 3 is locked by the stop 8—wedge 9 system. After setting the matrix 3 to the dimension of the cutting area 25 of the joint by turning it around the tool's axis of symmetry with the widened part of the shaft 4 with incisions facilitating gripping, its movement is locked by screwing in the stop 8 into the threaded hole 15 located in the matrix 3. Screwing in the stop 8 results in the gradual driving of the bottom surface of the wedge 9 into the non-threaded surface of the shaft 4. Gradual screwing in of the stop 8 at some point becomes impossible, which means that the wedge 9 resting against the surface of the shaft 4 has completely locked the movement of the system of the stop 8 with the matrix 3 In order to release the movement of the matrix 3 the stop 8 should be screwed out of it. The matrix 3 moves within the chamber of the body 1 limited by the walls of the body 1 and two parts of the cover 5 of the body 1. The cover 5 of the body 1 restricts the maximum external protraction of the matrix 3, additionally stabilising the position of the matrix 3 in relation to the tool's axis of symmetry. The cover 5 of the body 1 is bolted to the body 1 with a set of four mounting bolts 7. The rotational and linear movement of the matrix 3 in relation to the shaft 4 causes the head of the matrix 3 to press on the spherical ends of the cutting blades 16 of the burr 2. The ends of the cutting blades 16 of the burr 2 in the shape of the ball-shaped pivot 10 set on the threader rod and screwed into the body 1 move within the channels 12 cut in the surface of the head of the matrix 3. The guides 11 are cut symmetrically or asymmetrically in relation to the tool's axis of rotation—this depends, among others, on the number of cutting blades 16. The guides 11 restrict the movement of the cutting blades 16. Screwing the matrix 3 out of the body 1 in relation to the shaft 4 results in the cutting blades 16 of the burr 2 sliding into the closed chamber of the body 1 at an angle of 45°. Screwing the matrix 3 in has a reverse effect. The cutting blades 16 of the burr 2 slide out, making the cutting blades 16 closer to each other, which results in the decrease of the final diameter of the machined spherical surface 26. The movement of the cutting blades 16 of the burr 2 outside of the guides 11 cut in the head of the matrix 3 takes place within the space restricted by the openings 15 in the body 1. Channels 12 ensure the movement of the cutting blades 16 of the burr 2 over an arc-shape trajectory with a defined radius. After establishing an appropriate diameter of machining—that is, the position of the cutting blades 16 of the burr 2 and locking the movement of the matrix 3 with the stop 8, the drive mechanism 6 is used to provide rotational movement from an external drive. The cutting edges 16 of the burr 2 penetrate the material to the set diameter. The angle of application α of the cutting surface 25 of the cutting blades 16 of the matrix 3 has a value of 10°, and the bevel angle β 45°. The cuttings fall into the ducts 24 of the burr, falling out between the internal chamber 21 and the supporting surface 27 of the body 1 through the outlet opening 23 used to clean the inside of the burr 2. Along the shaft 4 and through the drive mechanism 6 a duct for a medium 20 (e.g. water) passes, which enables the delivery of a medium to the internal space of the body 1, diluting the cuttings and aiding in their removal.

After establishing the position (cutting diameter) of the matrix 3, the matrix 3 is locked by screwing in the stop 8 with the wedge 9, after which the drive is started. Afterwards, the tool is applied to the machined surface, e.g. the hip joint, and the medium is fed through the duct 20 located along the shaft 4 and in the drive mechanism 6, after which the surface is cut with the cutting blades 16 of the burr 2. The cuttings with the medium fall out through the outlet openings 23 of the burr ducts 24. Bigger pieces of the cuttings are broken by the cutting tongue 19. After removing a specified amount of matter from the hip joint the position of the matrix 3 is corrected by unlocking the clamp of the drive mechanism 6. After making the changes, inspecting the machined surface, e.g. the hip joint after removing another layer of the hip joint tissue, the matrix 3 is locked again and the material is again removed until required hip joint surface is obtained. The cutting area is limited on the outside by the cutting edges of the tool, and on the inside by the supporting surface 27, protecting against cortical tissue damage during the cutting process. Within the area of the supporting surface 27 the cutting process does not take place.

The invention claimed is:

1. An apparatus for use with a drive mechanism for reaming a surface of an acetabulum or a femoral head of a hip joint, the apparatus comprising:
    an outer body adapted to be connected by a joint to said drive mechanism so as to be rotatably driven by the drive mechanism, said outer body having a channel;
    at least one burr comprising:
        a slanting end;
        an arc shape;
        a cutting blade at a first end thereof; and
        a ball-shaped pivot at an opposite end thereof;
    an inner body having at least one guide, the ball-shaped pivot received in the at least one guide of said inner body;
    a shank having said inner body affixed at an end thereof; and
    a shaft connected by a threaded connection to said shank, the threaded connection having a lock member thereon, said outer body having a threaded joint secured to said shaft, said outer body having a chamber formed at an end thereof, the chamber adapted to receive a head of machined bone therein.

2. The apparatus of claim 1, wherein said outer body has an external supporting surface, the external supporting surface adapted to be inserted into the acetabulum.

3. The apparatus of claim 1, wherein the at least one burr is positioned at an angular distance from a plane perpendicular to a lengthwise axis of said cutting blade.

4. The apparatus of claim 1, wherein the at least one burr is beveled at an angle of between 40° and 50°.

5. The apparatus of claim 1, wherein the at least one burr has a cutting edge, the cutting edge having a cutting tongue.

6. An apparatus for use with a drive mechanism for reaming a surface of an acetabulum or a femoral head of a hip joint, the apparatus comprising:
    an outer body adapted to be connected by a joint to the drive mechanism so as to be rotatably driven by the drive mechanism, said outer body having a channel;
    at least one burr comprising:
        a slanting end;
        an arch shape;
        a cutting blade at a first end thereof; and
        a ball-shaped pivot at an opposite end thereof;
    an inner body having at least one guide, the ball-shaped pivot received in the at least one guide of said inner body;
    a shank having said inner body affixed at an end thereof; and
    a shaft connected by a threaded connection to said shank, the threaded connection having a lock member thereon, said body having a threaded joint secured to said shaft, wherein the at least one burr is a tube.

7. The apparatus of claim 6, wherein each tube has an open end.

8. The apparatus of claim 6, wherein each tube has a partially open end.

9. The apparatus of claim 6, wherein the at least one burr has an outlet opening, each outlet opening adapted to allow a cleaning of the at least one burr.

* * * * *